United States Patent
Cho et al.

(10) Patent No.: US 12,150,816 B2
(45) Date of Patent: Nov. 26, 2024

(54) MEDICAL-SURGICAL DEVICE HAVING TOOL MOVEMENT DISTANCE DISPLAY FUNCTION

(71) Applicant: CUREXO, INC., Seoul (KR)

(72) Inventors: Gyu Il Cho, Seoul (KR); Bong Oh Kim, Seoul (KR); Soo Jong Kim, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 18/609,380

(22) Filed: Mar. 19, 2024

(65) Prior Publication Data

US 2024/0315796 A1    Sep. 26, 2024

(30) Foreign Application Priority Data

Mar. 24, 2023 (KR) .......................... 10-2023-0038819

(51) Int. Cl.
*A61B 90/00* (2016.01)
*A61F 2/46* (2006.01)

(52) U.S. Cl.
CPC ............ *A61B 90/08* (2016.02); *A61F 2/4609* (2013.01); *A61B 2090/0807* (2016.02); *A61F 2002/4658* (2013.01); *A61F 2002/4681* (2013.01)

(58) Field of Classification Search
CPC ......... A61B 2090/061; A61B 2090/062; A61F 2002/4658; A61F 2002/4662
See application file for complete search history.

(56) References Cited

U.S. PATENT DOCUMENTS

| | | | | |
|---|---|---|---|---|
| 9,931,059 | B2 * | 4/2018 | Borja | A61B 5/1077 |
| 10,092,365 | B2 * | 10/2018 | Seeber | A61B 34/30 |
| 10,206,750 | B2 * | 2/2019 | Hagag | A61F 2/4609 |
| 2010/0137871 | A1 * | 6/2010 | Borja | A61F 2/4657 |
| | | | | 606/86 R |
| 2011/0082587 | A1 * | 4/2011 | Ziaei | A61B 34/30 |
| | | | | 700/260 |
| 2012/0184965 | A1 * | 7/2012 | Burgi | A61F 2/4609 |
| | | | | 606/99 |
| 2015/0272478 | A1 * | 10/2015 | Borja | A61B 5/1079 |
| | | | | 606/102 |
| 2020/0197192 | A1 * | 6/2020 | Greendyk | A61F 2/4611 |

(Continued)

FOREIGN PATENT DOCUMENTS

| | | |
|---|---|---|
| KR | 10-2013-0125861 A | 11/2013 |
| KR | 10-2016-0039695 A | 4/2016 |

(Continued)

*Primary Examiner* — Zade Coley
(74) *Attorney, Agent, or Firm* — Bridgeway IP Law Group, PLLC; Jihun Kim

(57) ABSTRACT

A medical-surgical device having a tool movement distance display function, indicates a target movement distance of a tool accurately and quickly during a surgical process, thereby not only improving the accuracy of surgery but also shortening surgery time and improving convenience of surgery. The medical-surgical device having the tool movement distance display function includes: a medical tool including a tool shaft; a holder body internally formed with a tool mounting hole to insert the medical tool therein; a tool support unit configured to support the medical tool inserted in the holder body; and a movement distance indicator configured to indicate a movement distance of the medical tool.

8 Claims, 19 Drawing Sheets

(56) References Cited

U.S. PATENT DOCUMENTS

2020/0323543 A1\* 10/2020 Carusillo ............... A61B 90/06
2022/0313455 A1\* 10/2022 van der Walt ........ A61F 2/4684

FOREIGN PATENT DOCUMENTS

| KR | 10-1609281 B1 | 4/2016 |
| KR | 10-2020-0115518 A | 10/2020 |
| KR | 10-2415277 B1 | 6/2022 |

\* cited by examiner

MEDICAL-SURGICAL DEVICE HAVING TOOL MOVEMENT DISTANCE DISPLAY FUNCTION

CROSS-REFERENCE TO RELATED APPLICATION

This application is based on and claims priority under 35 U.S.C. § 119 to Korean Patent Application No. 10-2023-0038819 filed on Mar. 24, 2023 in the Korean Intellectual Property Office, the disclosure of which is incorporated by reference herein in its entirety.

BACKGROUND

Field

The disclosure relates to a medical-surgical device having a tool movement distance display function, and more particularly to a medical-surgical device having a tool movement distance display function, which indicates a target movement distance of a tool accurately and quickly during a surgical process, thereby not only improving the accuracy of surgery but also shortening surgery time and improving the convenience of surgery.

Description of the Related Art

In general, surgical treatment for joint diseases includes arthroscopic surgery, chondrocyte transplantation, etc., and includes artificial joint surgery for severe conditions. As representative artificial joint surgery, there are manual artificial joint surgery manually performed by medical personnel, and robotic artificial joint surgery performed by a robot.

Robotic artificial joint surgery refers to a surgical procedure of placing an artificial joint (implant) after cutting a bone in a joint site by rotating a cutter of a cutting device mounted to a distal end of a position-variable arm of the robot based on information input to a computer and employs a cutting tool such as a drill, a reamer for widening a hole, an impactor for providing impaction.

As artificial joint surgery, artificial knee joint surgery has already become common, and artificial hip joint surgery has recently also become increasingly common.

Artificial hip joint surgery is typically performed by preprocessing an acetabulum of a hip joint using the reamer, inserting an artificial acetabulum cup, pressing and fixing the artificial acetabulum cup using the impactor, and connecting an artificial femoral head. In this case, the artificial acetabulum cup is larger than the diameter of the acetabulum preprocessed by the reamer and thus inserted by the impaction using the impactor.

Meanwhile, the foregoing reamer includes a straight reamer having an outer appearance of a straight structure, and a curved reamer having an outer appearance of a curved structure and called an offset reamer.

In addition, the impactor includes a straight impactor handle having an outer appearance of a straight structure, and a curved impactor handle having an outer appearance of a curved structure.

Meanwhile, the foregoing impactor such as the straight impactor handle and the curved impactor handle is used by medical personnel to apply striking force thereto as being installed in a medical tool holder while the surgery is performed.

Further, technology for the medical tool holder has been proposed in Korean Patent No. 10-1609281 (registered on Mar. 30, 2016), titled 'TOOL, KIT-OF-PARTS FOR MULTI-FUNCTIONAL TOOL, AND ROBOTIC SYSTEM FOR SAME.'

The tool mounted to the end of the robot arm, disclosed in Korean Patent No. 10-1609281, allows medical personnel to perform the artificial hip joint surgery by striking the impactor but has limitations that involve problems as follows.

For example, the tool disclosed in Korean Patent No. 10-1609281 employs the impactor to press and install the artificial acetabulum cup to the acetabulum of the hip joint as described above, but there is no way to check whether the artificial acetabulum cup has been inserted up to a set target point of the acetabulum, which is an obstacle to stable surgery, thereby causing disadvantages of not only lowering the quality of surgery and increasing surgery time but also increasing the fatigue of medical personnel.

In particular, the diameter of the artificial acetabulum cup is usually larger than the diameter of the acetabulum, and it is thus impossible to accurately measure the insertion depth of the acetabulum due to factors such as the impactor being pushed backward if the striking force and the position are not accurately set, thereby making it further difficult to perform accurate surgery.

DOCUMENTS OF RELATED ART

Patent Document (Patent Document 1) Korean Patent Publication No. 10-2020-0115518, titled "END EFFECTORS, SYSTEMS, AND METHODS FOR IMPACTING PROSTHETICS GUIDED BY SURGICAL ROBOTS"

SUMMARY

The disclosure is proposed based on the foregoing content, and an aspect of the disclosure is to provide a medical-surgical device having a tool movement distance display function, which indicates a target movement distance of a tool accurately and quickly during a surgical process, thereby not only improving the accuracy of surgery but also shortening surgery time and improving the convenience of surgery.

According to an embodiment of the disclosure, a medical-surgical device having a tool movement distance display function includes a medical tool including a tool shaft; a holder body internally formed with a tool mounting hole to insert the medical tool therein; a tool support unit configured to support the medical tool inserted in the holder body; and a movement distance indicator configured to indicate a movement distance of the medical tool.

The movement distance indicator may include: a movement distance-detecting displacement portion formed in the tool shaft and interlocking with the tool shaft; and a movement distance display unit detecting and displaying displacement of the movement distance-detecting displacement portion.

The movement distance-detecting displacement portion may be formed in the tool shaft and structured to have a distance-detecting slope of which a diameter gradually increases in the forward direction of the medical tool.

The movement distance display unit may be installed in the holder body so that a measuring end thereof can move in contact with the distance-detecting slope, and may include a distance-indicating gauge that displays a movement distance corresponding to the height of the distance-detecting slope.

The distance indicating gauge may include an analog dial gauge that includes a stem provided with a spindle including a measuring stylus at an end thereof, a pointer coupled to the stem and rotating based on a retraction degree of the measuring stylus, and a display housing including a scale plate on which the pointer rotates; or a digital gauge (not shown) that includes a stem provided with a retractable measuring stylus, and a display displaying digits based on a retraction degree of the measuring stylus.

The holder body may be formed with a coupling boss that communicates with the tool mounting hole so that the stem can be installed at a position corresponding to the movement distance-detecting displacement portion.

The movement distance indicator may include a shaft scale portion formed on an exposed portion of the tool shaft of the medical tool inserted in the holder body and include a plurality of scales.

The shaft scale portion may be formed to be positioned on a surface of the tool shaft on the rear side of the holder body, and configured to be set by aligning the corresponding scales with a rear end portion of the holder body upon setting a desired target movement distance of the medical tool.

The medical tool may be configured as an impactor used for hip surgery by having an artificial acetabular cup coupled to the front of the tool shaft and a striking portion provided at the rear thereof to which striking force is applied.

The tool support unit may include a tool support guide member to guide the movement of the tool shaft while supporting the tool shaft.

According to the disclosure, the medical-surgical device having the tool movement distance display function may include a holder support member coupled to the holder body, wherein the tool mounting hole includes a guide member installation groove formed on the inner circumferential surface thereof to seat the tool support guide member therein, a support member installation groove formed adjacent to the guide member installation groove so that a holder binding member for the installation of the holder support member can be installed, and a tool installation groove formed in an end portion of the tool mounting hole on a first side to install the medical tool therein.

In addition, according to the disclosure, the medical-surgical device having the tool movement distance display function may include a shock reduction device installed in the holder body to absorb and cushion a shock applied to the holder body; and a shock reduction device insertion portion formed in an end portion of the tool mounting hole of the holder body on a second side to install the shock reduction device.

Further, according to the disclosure, the medical-surgical device having the tool movement distance display function may include a tool binding unit configured to bind the medical tool inserted in the tool installation groove, wherein the tool binding unit includes a binding hole perforated in the holder body to communicate with an inside of the tool installation groove, a tool binding member inserted through the binding hole, and a locking portion formed in the medical tool and allowing the tool binding member to be inserted and locked thereinto.

BRIEF DESCRIPTION OF THE DRAWINGS

The above and/or other aspects will become apparent and more readily appreciated from the following description of embodiments, taken in conjunction with the accompanying drawings, in which:

FIGS. 10A to 10H are views to illustrate a shock reduction device in a medical-surgical device having a tool movement distance display function according to an embodiment of the disclosure, in which FIG. 10A is an exploded perspective view, FIG. 10B is a perspective view to illustrate the internal structure, FIG. 10C is a lateral view, FIG. 10D is an enlarged view of an elastic member, FIG. 10E is an enlarged view of a separation preventing member, and FIG. 10F is a partial cut-open perspective view, and FIGS. 10G and 10H are views to illustrate the use states of the shock reduction device, in which FIG. 10G is a partially enlarged view to illustrate a state of when a hammer normally strikes a striking portion of an impactor, and FIG. 10H is a partially enlarged view to illustrate a state of when the hammer misses the striking portion of the impactor.

DETAILED DESCRIPTION OF EMBODIMENTS

Figure 1:
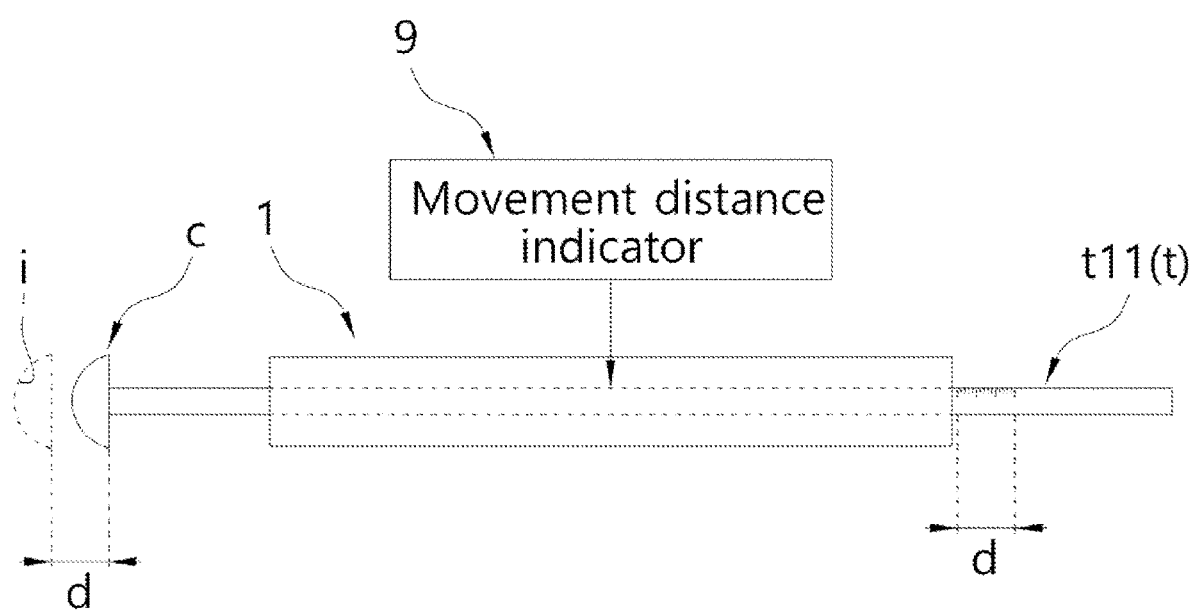
FIG. 1 is a schematic configuration view to illustrate a technical idea of a medical-surgical device having a tool movement distance display function according to an embodiment of the disclosure.

Below, exemplary embodiments of the disclosure will be described in detail with reference to the accompanying drawings, wherein the same components will be described by the same reference numerals.

Meanwhile, detailed descriptions of elements and their operations and effects, which are easily understood by a person having ordinary knowledge of the art from general technology, in the accompanying drawings will be simplified or omitted. In addition, the disclosure is characterized in a medical-surgical device having a tool movement distance display function, and thus illustration and description will be made focusing on related parts while simplifying or omitting the other parts. The medical-surgical device having the tool movement distance display function according to an embodiment of the disclosure may be used to measure a movement distance while holding various medical tools applied to surgical operations or the like, but it will be described below by way of example that the medical-surgical device is applied to an impactor used in artificial hip joint surgery. Further, front and forward directions refer to a direction in which a medical tool faces toward a surgical site, and rear and backward directions refer to a direction opposite to the front direction.

Figure 2:
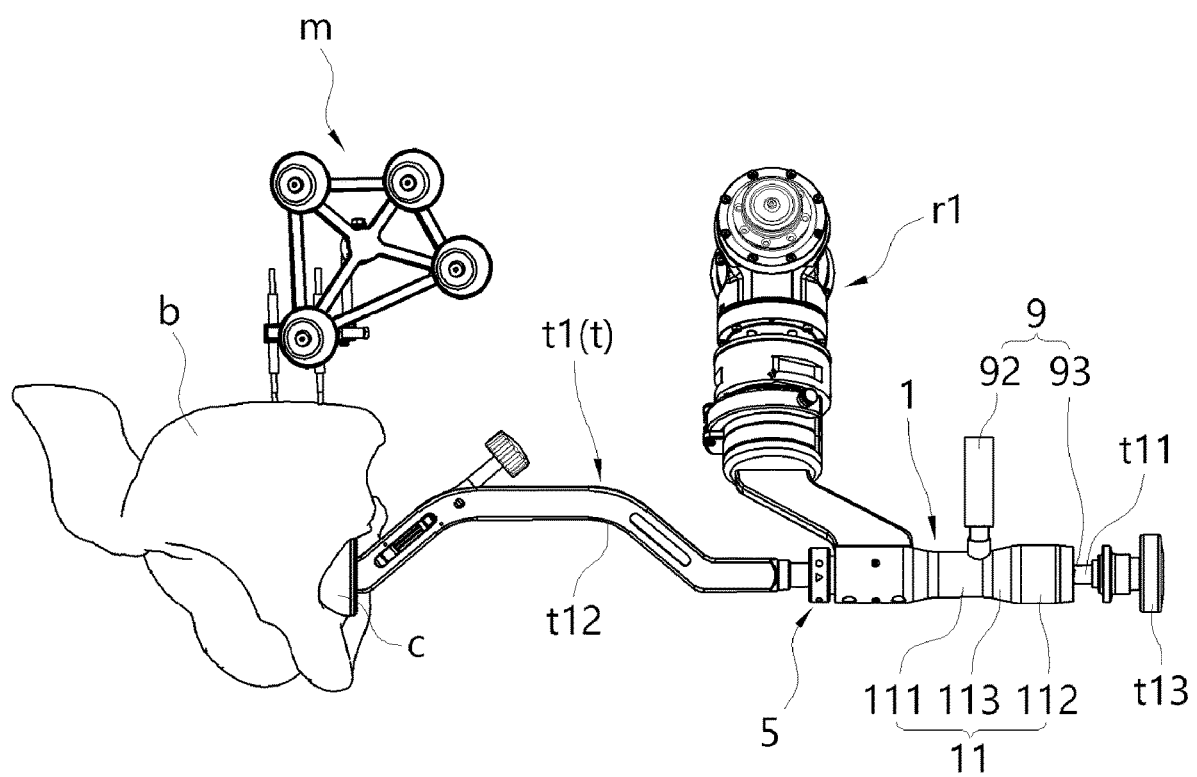
FIG. 2 is an overall configuration view of a medical-surgical device having a tool movement distance display function according to an embodiment of the disclosure.
Figure 3:
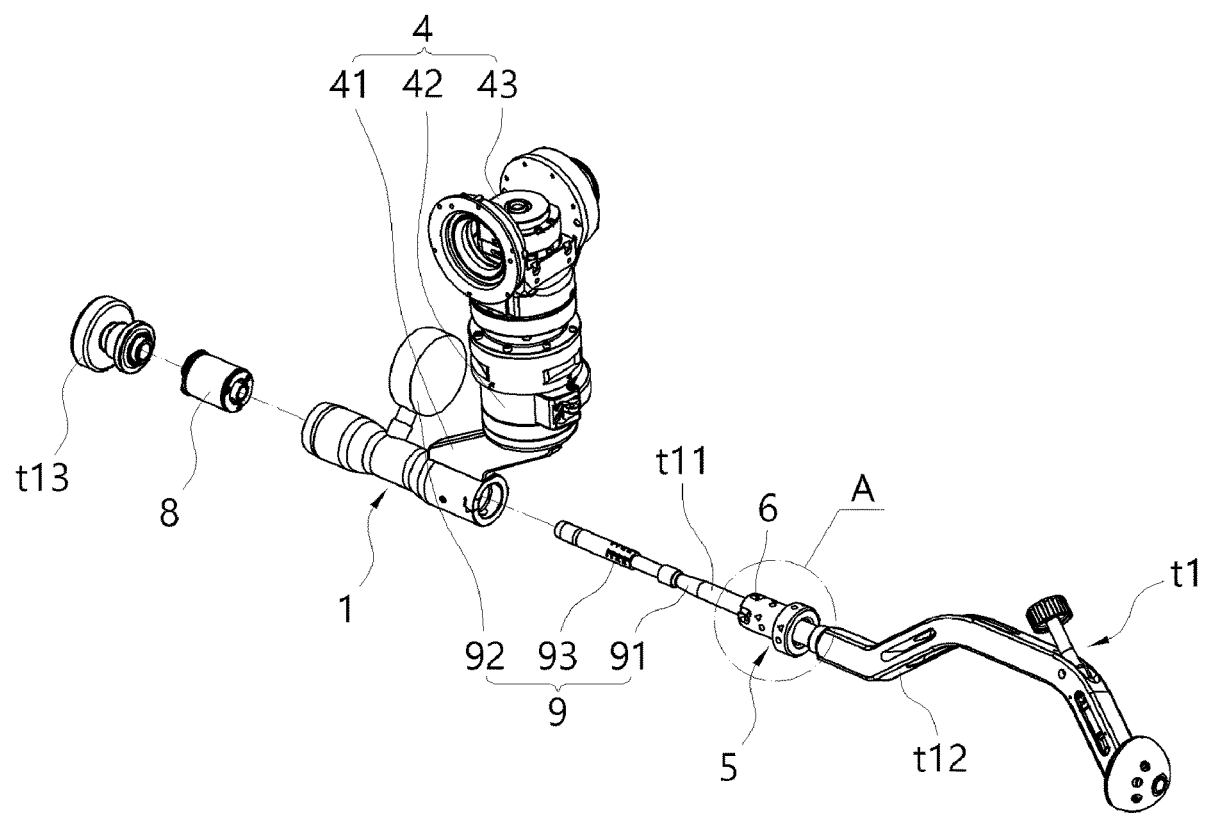
FIG. 3 is an exploded perspective view of the main elements in a medical-surgical device having a tool movement distance display function according to an embodiment of the disclosure.
Figure 4:
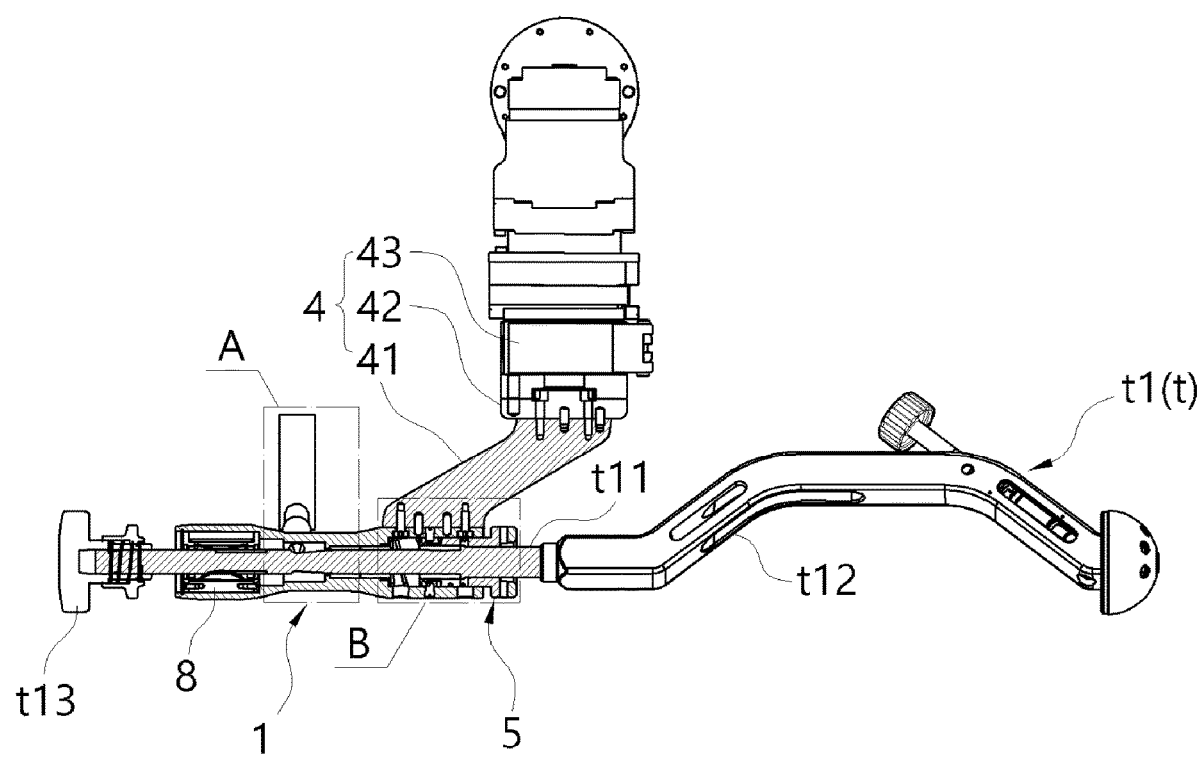
FIG. 4 is a cross-sectional view of a medical-surgical device having a tool movement distance display function according to an embodiment of the disclosure.
Figure 5:
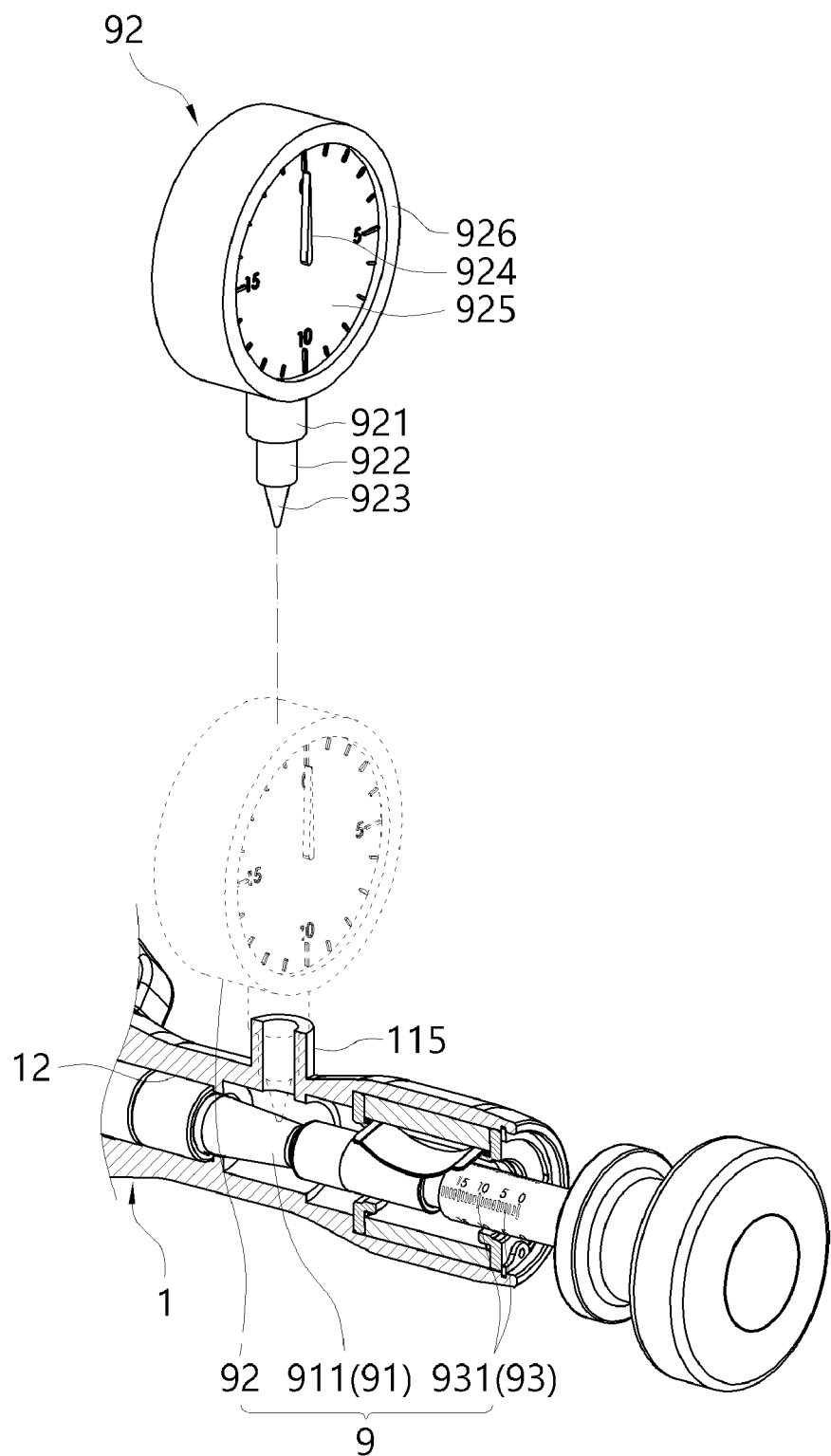
FIG. 5 is a cut-open perspective view of a main part of a medical-surgical device having a tool movement distance display function according to an embodiment of the disclosure.
Figure 6:
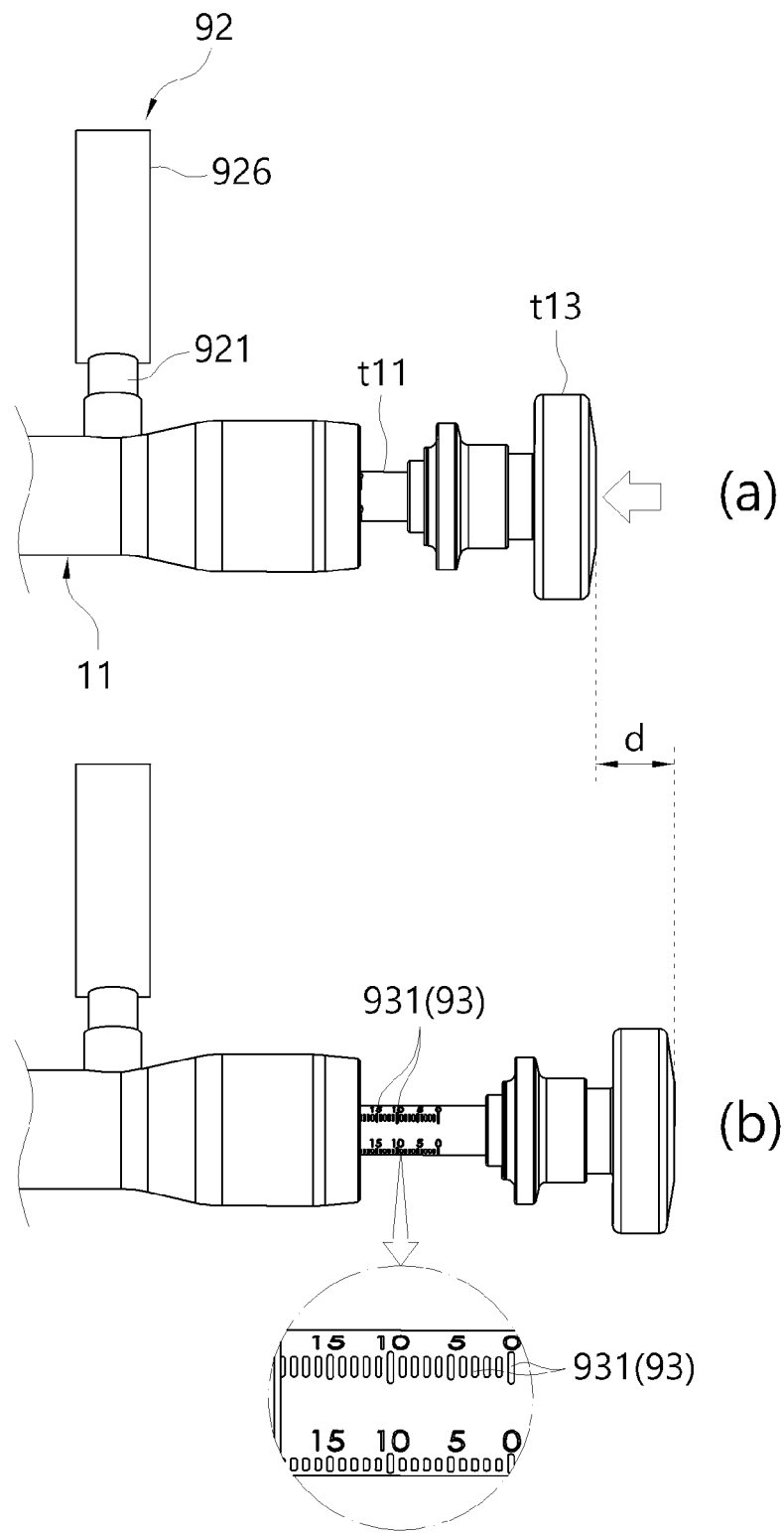
FIG. 6 is a view to illustrate the operating states of a medical-surgical device having a tool movement distance display function according to an embodiment of the disclosure, in which (a) shows a state that the artificial acetabulum cup is completely inserted, and (b) shows a state that a target position (i.e., impacting depth) of the artificial acetabulum cup is set.

FIG. 1 is a schematic configuration view to illustrate a technical idea of a medical-surgical device having a tool movement distance display function according to an embodiment of the disclosure, and FIG. 2 is an overall configuration view of a medical-surgical device having a tool movement distance display function according to an embodiment of the disclosure, which is a perspective view schematically showing use states of the medical-surgical device. FIG. 3 is an exploded perspective view of the main elements in a medical-surgical device having a tool movement distance display function according to an embodiment of the disclosure, and FIG. 4 is a cross-sectional view of a medical-surgical device having a tool movement distance display function according to an embodiment of the disclosure. FIG. 5 is a cut-open perspective view of a main part of a medical-surgical device having a tool movement distance display function according to an embodiment of the disclosure, which shows both mounted state and separated state of a distance indicating gauge. FIG. 6 is a view to illustrate the operating states of a medical-surgical device having a tool movement distance display function according to an embodiment of the disclosure, in which (a) shows a state that the artificial acetabulum cup is completely inserted, and (b) shows a state that a target position (i.e., impacting depth) of the artificial acetabulum cup is set.

Referring to FIGS. 1 to 6, a medical-surgical device having a tool movement distance display function according to an embodiment of the disclosure is to improve the accuracy of surgery by indicating the movement distance of a tool accurately and conveniently during a surgical process, and is, in particular, characterized in that depth at which an artificial acetabulum cup is inserted in a pelvic bone up to a target insertion position i is easily recognized during artificial hip joint surgery.

The medical-surgical device having a tool movement distance display function according to an embodiment of the disclosure includes a medical tool t having a tool shaft t11, a holder body 1 internally formed with a tool mounting hole to insert the medical tool t therein, a tool support unit 2 supporting the medical tool t inserted in the holder body, a tool binding unit 3 for binding the medical tool t to the holder body 1, and a holder support member 4 for installing the holder body 1 in an arm (not shown) of a medical robot, and further includes a movement distance indicator 9 for displaying a movement distance of the medical tool t for the recognition of the movement distance.

Here, the movement distance d refers to the distance to a set target position (impacting depth) of an artificial acetabulum cup c, or the remaining distance to the set target position i.

The movement distance indicator 9 includes a movement distance-detecting displacement portion 91 formed in the tool shaft t11 and interlocking with the tool shaft t11, and a movement distance display unit 92 detecting and displaying the displacement of the movement distance-detecting displacement portion 91.

In addition, there are no specific limits to the shape or structure of the movement distance indicator 9 as long as it includes the movement distance-detecting displacement portion 91 and the movement distance display unit 92 to effectively indicate the movement distance of the tool shaft t11. According to this embodiment, the movement distance indicator 9 is structured to detect and indicate the movement distance based on mechanical contact to ensure reliability as follows.

For example, the movement distance-detecting displacement portion 91 is formed in the tool shaft t11 and structured to have a distance-detecting slope 911, the diameter of which gradually increases in the forward direction of the medical tool t1.

In addition, there are no specific limits to the shape, structure, etc. of the movement distance-detecting displacement portion 91 as long as it has the distance-detecting slope 911. According to this embodiment, the movement distance-detecting displacement portion 91 is approximately shaped like a cone. In this case, the angle of the distance-detecting slope 911 is formed to move a pointer of a distance indicating gauge by 1 mm when the tool shaft t11 moves by 1 mm.

The movement distance display unit 92 is installed in the holder body 1 so that its measuring end can move in contact with the distance-detecting slope 911 and includes a distance-indicating gauge that displays a movement distance corresponding to the height of the distance-detecting slope 911.

The distance indicating gauge is implemented by an analog dial gauge that includes a stem 921 provided with a spindle 922 having a measuring stylus 923 at an end thereof, a pointer 924 coupled to the stem 921 and rotating based on a retraction degree (upward and downward movement) of the measuring stylus 923, and a display housing 926 including a scale plate 925 on which the pointer 924 rotates. In addition, the analog dial gauge includes a pointer actuator (not shown) internally provided in the display housing 926 including a spiral spring (not shown) and a gear system (not shown) such as a rack and a pinion to rotate the pointer 924 in response to the movement of the spindle 922. Such a pointer actuator is well known, and thus detailed illustration thereof is omitted.

Alternatively, although it is not illustrated in the accompanying drawings, the distance indicating gauge may also be implemented by a digital gauge (not shown) that includes a stem provided with a spindle having a measuring stylus at an end thereof, and a display coupled to the stem and displaying digits based on a retraction degree of a measuring stylus.

Further, the movement distance indicator 9 may be configured to transmit a detected movement distance to a surgical control terminal or a surgical robot controller.

The holder body 1 is, as shown in FIG. 5, formed with a protruding coupling boss 115 that communicates with a tool mounting hole 12 so that the stem 921 can be installed at the position corresponding to the movement distance-detecting displacement portion 91.

Meanwhile, the movement distance indicator 9 includes a shaft scale portion 93 formed on the medical tool t so that the movement distance of the tool shaft t11 can be recognized at various positions and double-checked together with the distance indicating gauge so as to be recognized without error.

The shaft scale portion 93 includes a plurality of scales 931 and Arabic numerals for indicating distances, which are marked on an exposure part of the tool shaft t11 of the medical tool t inserted in the holder body 1.

The shaft scale portion 93 is positioned on the tool shaft t11 on the rear side of the holder body 1 and may be pulled so that the scale corresponding to a desired target movement distance can be aligned with the rear end of the holder body 1 (i.e., the rear end line of the holder body 1) in order to set the desired target movement distance of the medical tool.

There are no specific limits to the medical tool t as long as it is a medical tool that has the tool shaft t11. According to this embodiment, an impactor t1 will be described as an example of the medical tool t. In addition, the impactor t1 may employ a straight impactor handle having the outer appearance of a straight structure. According to this embodiment, a curved impactor handle having the outer appearance of a curved structure will be described as an example of the impactor.

The curved impactor handle is approximately shaped like a rod and includes a tool shaft t11 having a straight structure to be inserted in the holder body 1, a tool curved portion t12 extending on the first side of the tool shaft t11, and a striking portion t13 provided at the end of the tool shaft on a second side and shaped like a cap to which a striking force of a hammer is applied upon surgery.

The curved impactor handle is provided with an impactor holding member 5 movably inserted in the tool shaft t11, coupled to a tool installation groove 15 of the holder body 1, and formed with a locking portion 33 (to be described later).

Figure 7A:
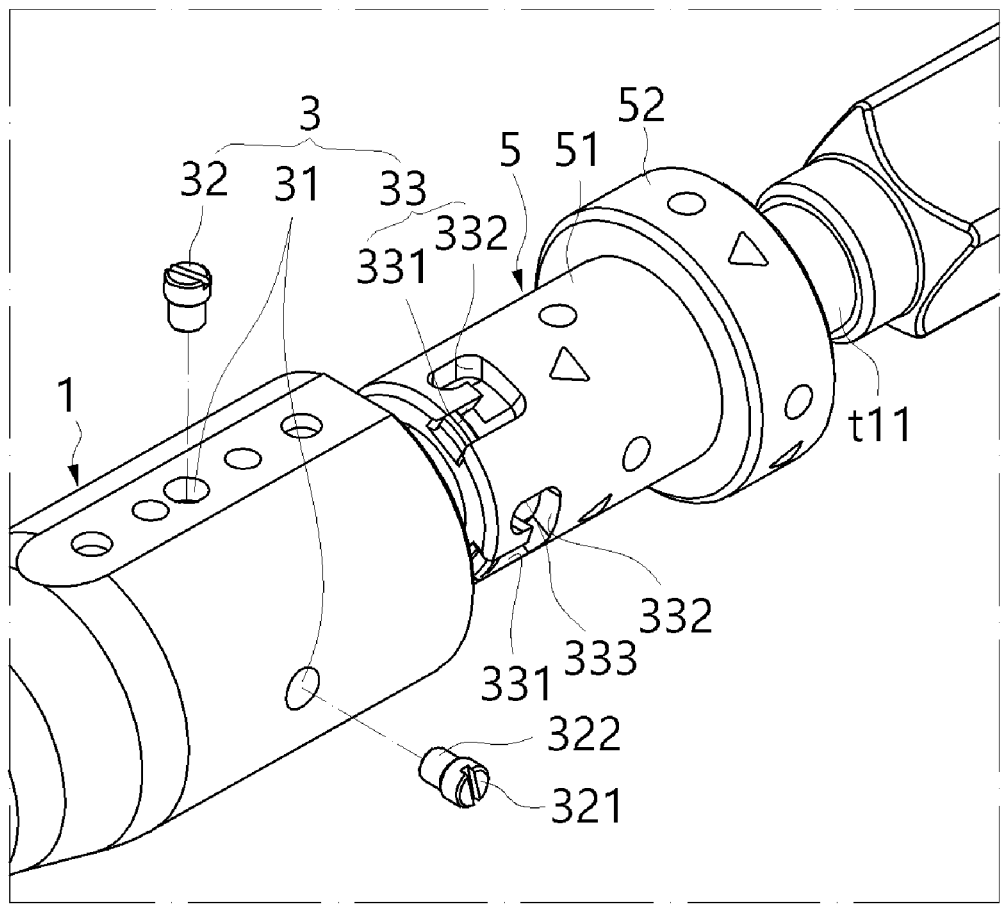
FIG. 7A is an exploded perspective view of a tool shaft portion "A" in FIG. 3.
Figure 7B:
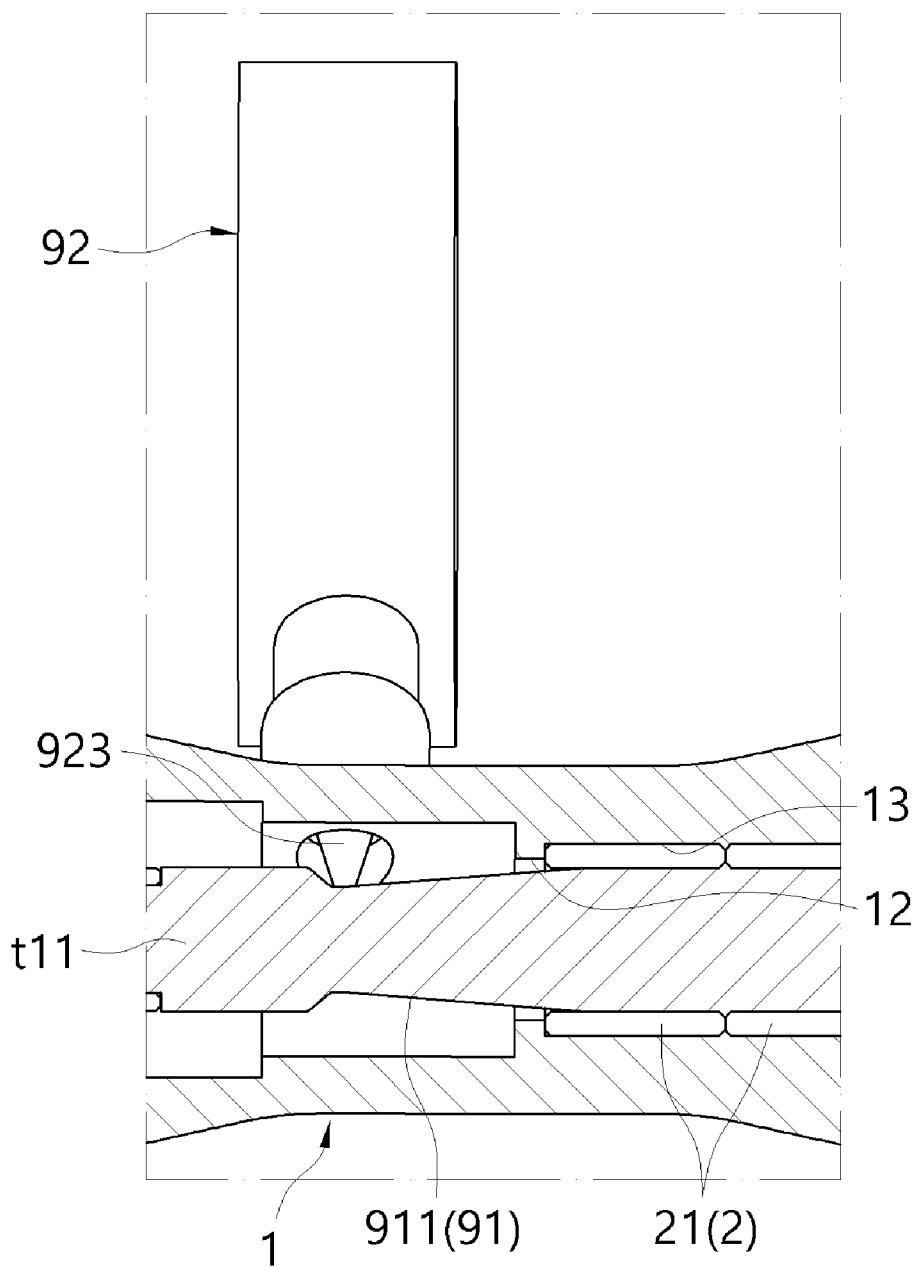
FIG. 7B is an enlarged view of "A" in FIG. 4.
Figure 7C:
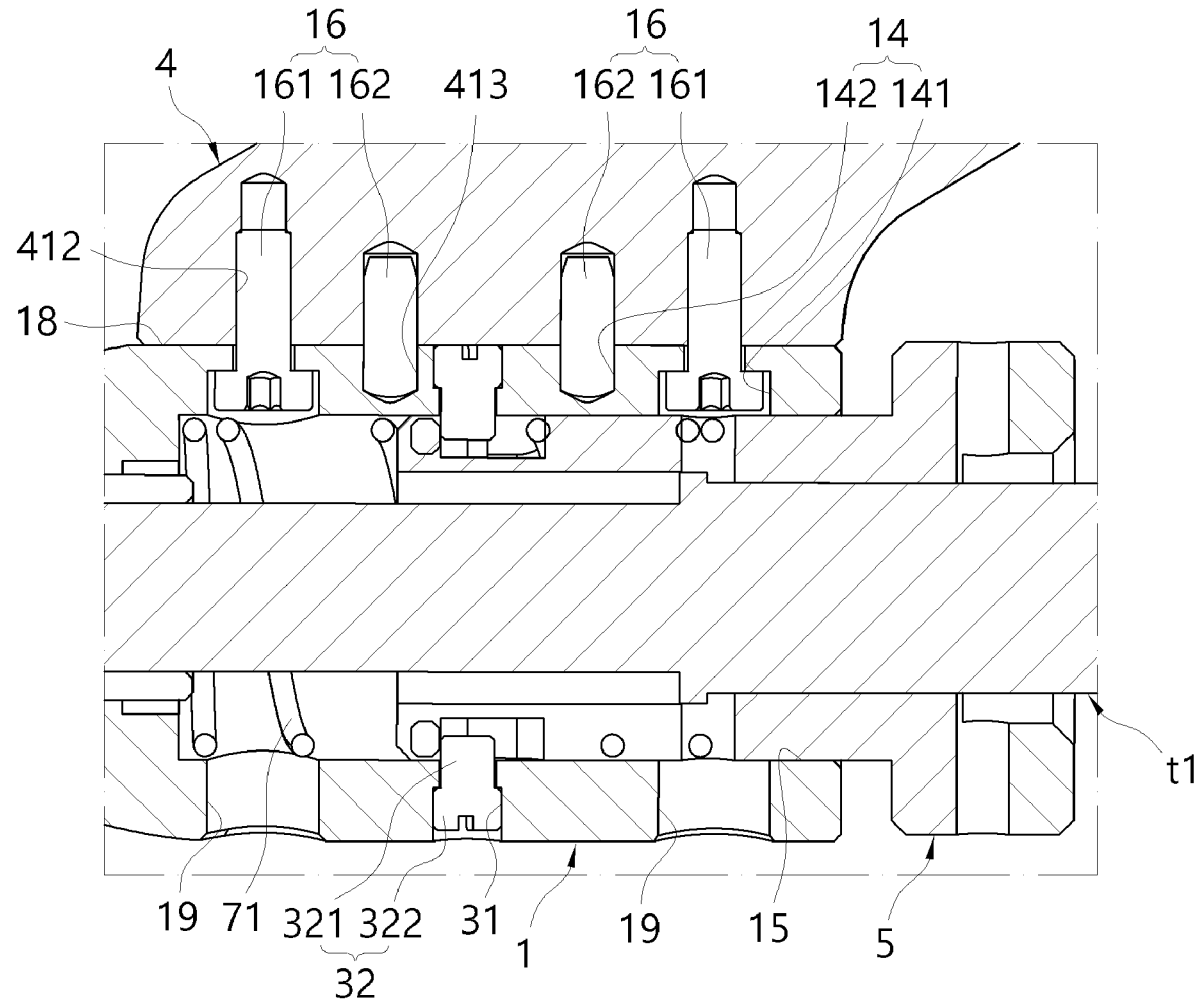
FIG. 7C is an enlarged view of "B" in FIG. 4.
Figure 8:
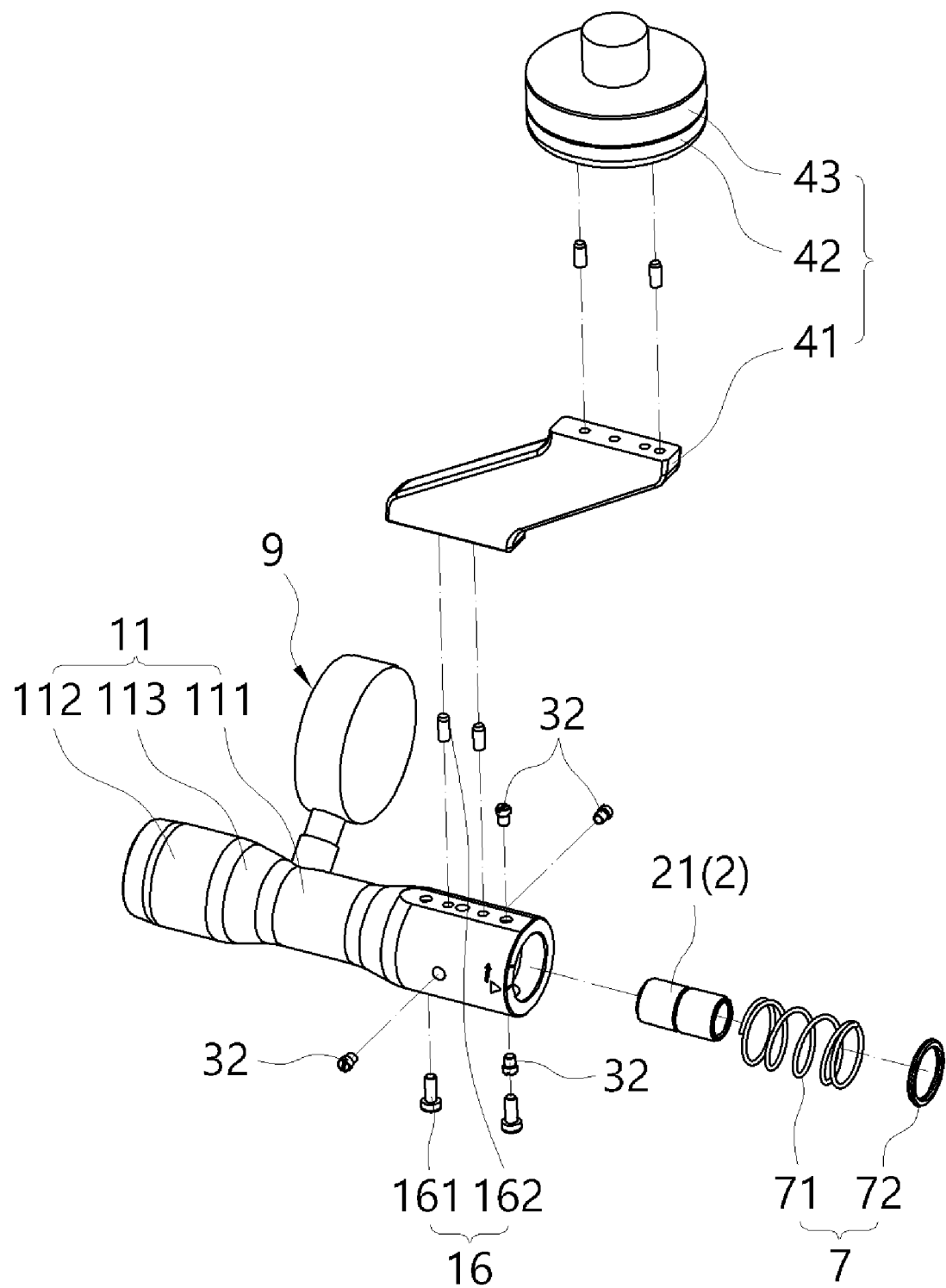
FIG. 8 is an exploded perspective view of a holder body portion in a medical-surgical device having a tool movement distance display function according to an embodiment of the disclosure.
Figure 9:
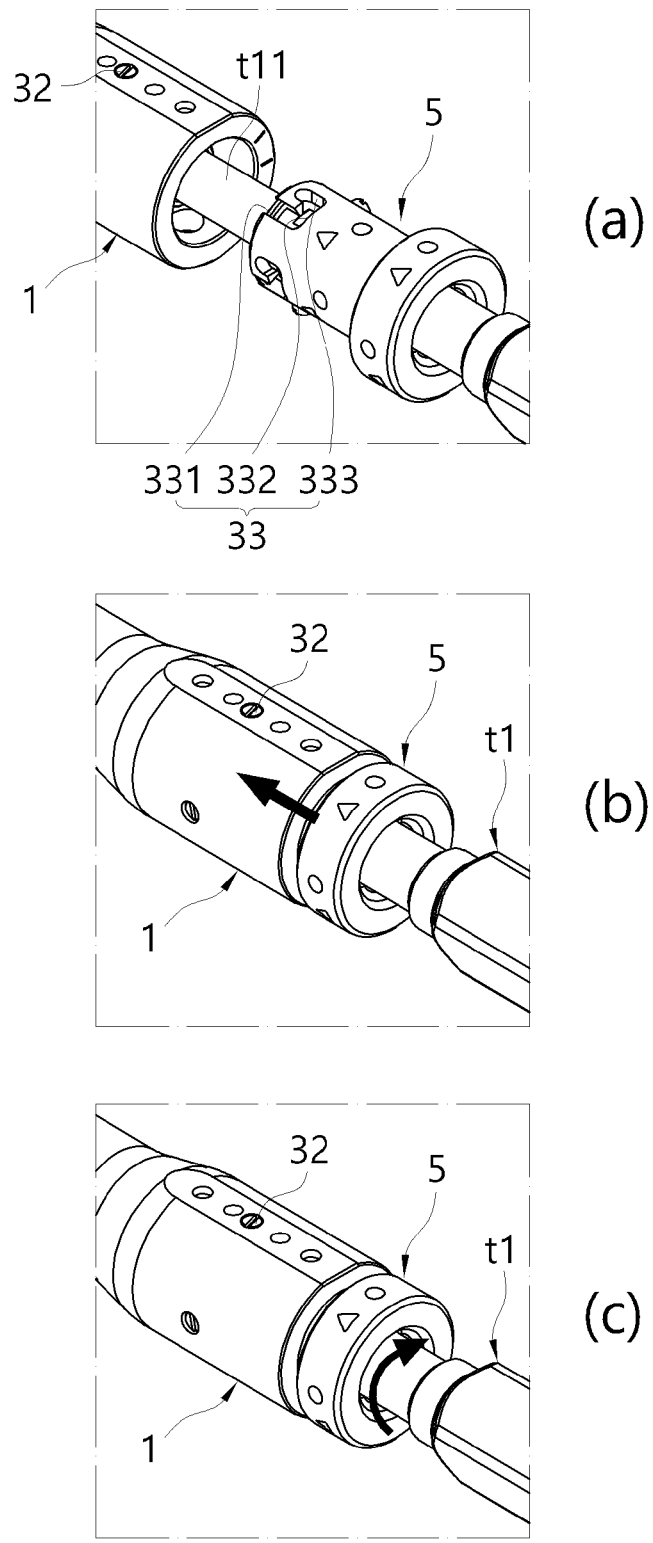
FIG. 9 is a view to illustrate a process of mounting a medical tool to a holder body in a medical-surgical device having a tool movement distance display function according to an embodiment of the disclosure.

FIG. 7A is an exploded perspective view of a tool shaft portion "A" in FIG. 3, FIG. 7B is an enlarged view of "A" in FIG. 4, and FIG. 7C is an enlarged view of "B" in FIG. 4. FIG. 8 is an exploded perspective view of a holder body portion in a medical-surgical device having a tool movement distance display function according to an embodiment of the disclosure, and FIG. 9 is a view to illustrate a process of mounting a medical tool to a holder body in a medical-surgical device having a tool movement distance display function according to an embodiment of the disclosure.

Referring to FIG. 7A, the impactor holding member 5 includes a cylindrical body 51 put on the tool shaft t11 and formed with the locking portion 33 (to be described later), and a stop ring 52 protruding on the outer side of the cylindrical body 51.

The holder body 1 refers to an element that functions as a housing to hold the medical tool t as shown in FIGS. 4 to 8, and is internally formed with a tool mounting hole 12 in a lengthwise direction to insert the medical tool in a hollow column body 11.

The hollow column body 11 includes a holder body 111 shaped like a pipe, a shock reduction device installation portion 112 formed in a rear portion of the holder body 111 and formed with a shock reduction device insertion portion having an inner diameter large enough to make an outer diameter portion of a shock reduction device 8 be forcibly fitted thereto, and a reducing portion 113 of which the inner diameter is reduced to prevent the shock reduction device 8 from being pushed backward even though external force is applied thereto.

As shown in FIGS. 7C and 8, the tool mounting hole 12 includes a guide member installation groove 13 formed on the inner circumferential surface thereof to seat a tool support guide member 21 therein, a support member installation groove 14 formed adjacent to the guide member installation groove 13 so that a holder binding member 16 for the installation of the holder support member 4 can be installed, and the tool installation groove 15 formed in the end portion of the tool mounting hole 12 on the first side to insert the medical tool therein.

The support member installation groove 14 includes a bolt insertion hole 141 having a bolt head insertion groove and a screw insertion groove to insert a bolt 161 (to be described later) therein, and a pin insertion hole 142 recessed adjacent to the bolt insertion hole 141.

The holder binding member 16 includes a bolt 161 inserted in the bolt insertion hole 141, and a stop pin 162 inserted between the holder support rod 41 and the holder body 1.

In addition, a bolt incoming hole 19, through which the bolt 171 is inserted to be fastened, is perforated on a lower side of the holder body 1 coaxially with the bolt insertion hole 141, and a road seating surface 18, on which the lower end of the holder support rod 41 is seated, is formed flatways.

Meanwhile, the tool support unit 2 refers to an element that supports the medical tool inserted in the holder body 1 and includes the tool support guide member 21 to support and guide the movement of the tool shaft t11.

The tool support guide member 21 is implemented by a sliding support body of which an outer circumferential surface is coupled to the inner circumferential surface of the guide member installation groove 13 provided in the tool mounting hole 12, and an inner circumferential surface allows the tool shaft t11 to be inserted therein. Here, the sliding support body may be implemented by a bearing. In this embodiment, a plurality of sliding bushes, usually called oilless bussing, is provided as an example of the sliding support body.

Meanwhile, the holder support member 4 refers to an element that has a first side coupled to the holder body 1 to perform a supporting function for the holder body 1, and a second side installed in the arm or the like of the medical robot.

The holder support member 4 includes the holder support rod 41 having a first end coupled to the holder body 1, a connecting plate 42 formed at a second end of the holder support rod 41, and an arm connecting member 43 bound to the connecting plate 42.

The holder support rod 41 refers to a member that is shaped like an inclined rod and fastened by foregoing bolt 161 and the stop pin 162 while the lower end thereof is seated on the road seating surface 18 of the holder body 1. The holder support rod 41 is formed with a bolt fastening hole 412 and a pin insertion hole 413 at positions corresponding to the bolt insertion hole 141 and the pin insertion hole 142.

Meanwhile, the tool binding unit 3 refers to an element that binds the medical tool t inserted in the tool installation groove 15 and is not specially limited as long as it can bind and release the medical tool. According to this embodiment, the tool binding unit 3 has a concise and simple structure and is configured so that various compatible medical tools can be detachably mounted thereto.

As shown in FIGS. 7A, 7C, and 8, the tool binding unit 3 includes a plurality of binding holes 31 perforated on the circumference of the holder body 1 to communicate with the inside of the tool installation groove 15, a tool binding member 32 inserted through the binding holes 31, and the locking portion 33 formed in the medical tool t and allowing the tool binding member 32 to be inserted and locked thereinto.

The tool binding member 32 includes a screw portion 321 fastened to the binding holes 31, and a locking protrusion 322 formed at the end portion of the screw portion 321 and inserted in the locking portion 33.

The locking portion 33 is formed in the impactor holding member 5 and includes an incoming groove 331 recessed at an inner end portion of the cylindrical body 51, and a locking groove 332 extending from the incoming groove 331 curvedly having an approximately 'L' shape.

The process of mounting the medical tool t using the foregoing tool binding unit 3 will be briefly described below with reference to FIG. 9. When the locking protrusion 322 of the tool binding member 32 is aligned with the incoming groove 331 as shown in (a) in FIG. 9, inserted into the incoming groove 331 by pressing the medical tool t1 inwards as shown in (b) of FIG. 9, and rotated at an angle of approximately 30 degrees along the locking groove 332 as shown in (c) of FIG. 9, the locking protrusion 322 enters a recessed end portion 333 of the locking groove 332 by the elasticity of an elastic pressurizer, thereby stably holding the medical tool t1 not to be separated.

Meanwhile, as shown in FIGS. 7A and 8, the tool installation groove 15 includes the elastic pressurizer 7 that applies the elasticity to stably bind the inserted medical tool t1.

The elastic pressurizer 7 includes a compression coil spring 71 to provide the elasticity to a portion of the medical tool t inserted in the tool installation groove 15 and a pressurization ring 72 to pressurize the medical tool with the elasticity applied from the compression coil spring 71.

Figure 10A:
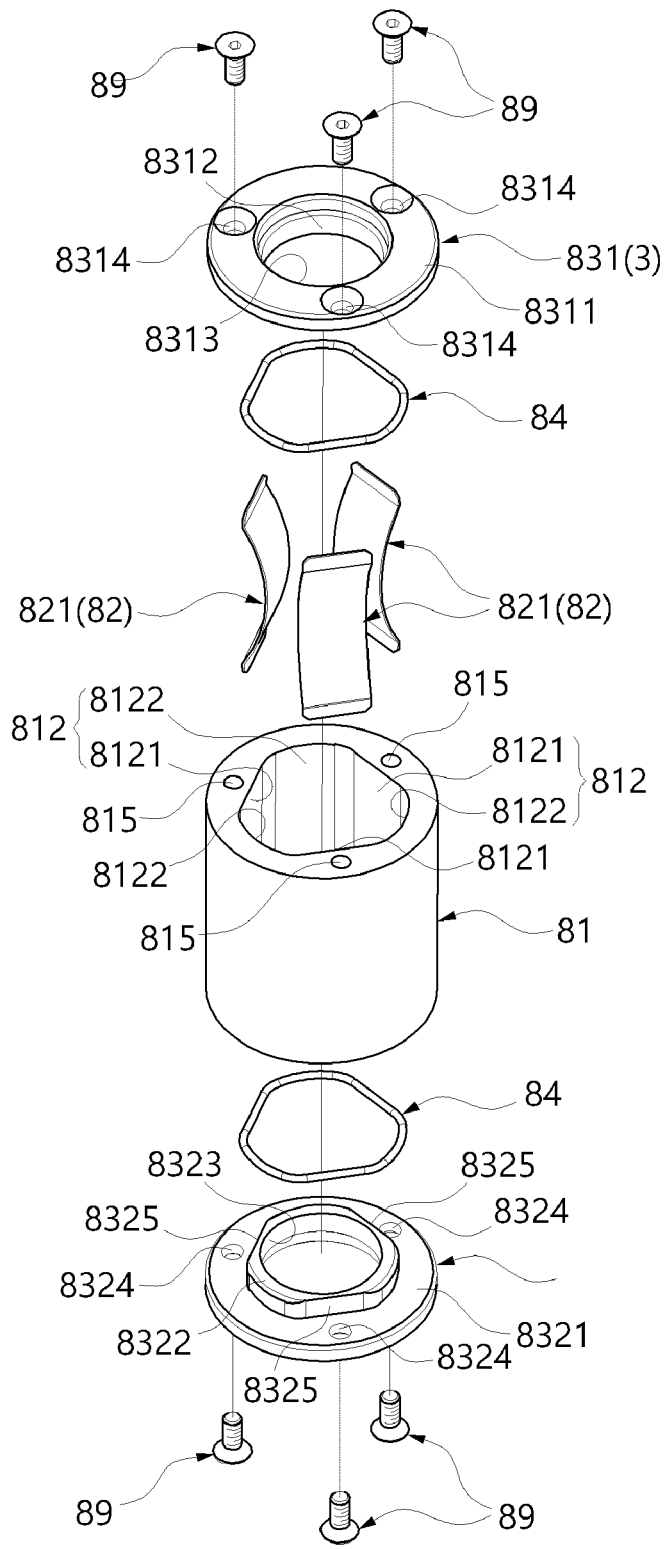
Figure 10B:
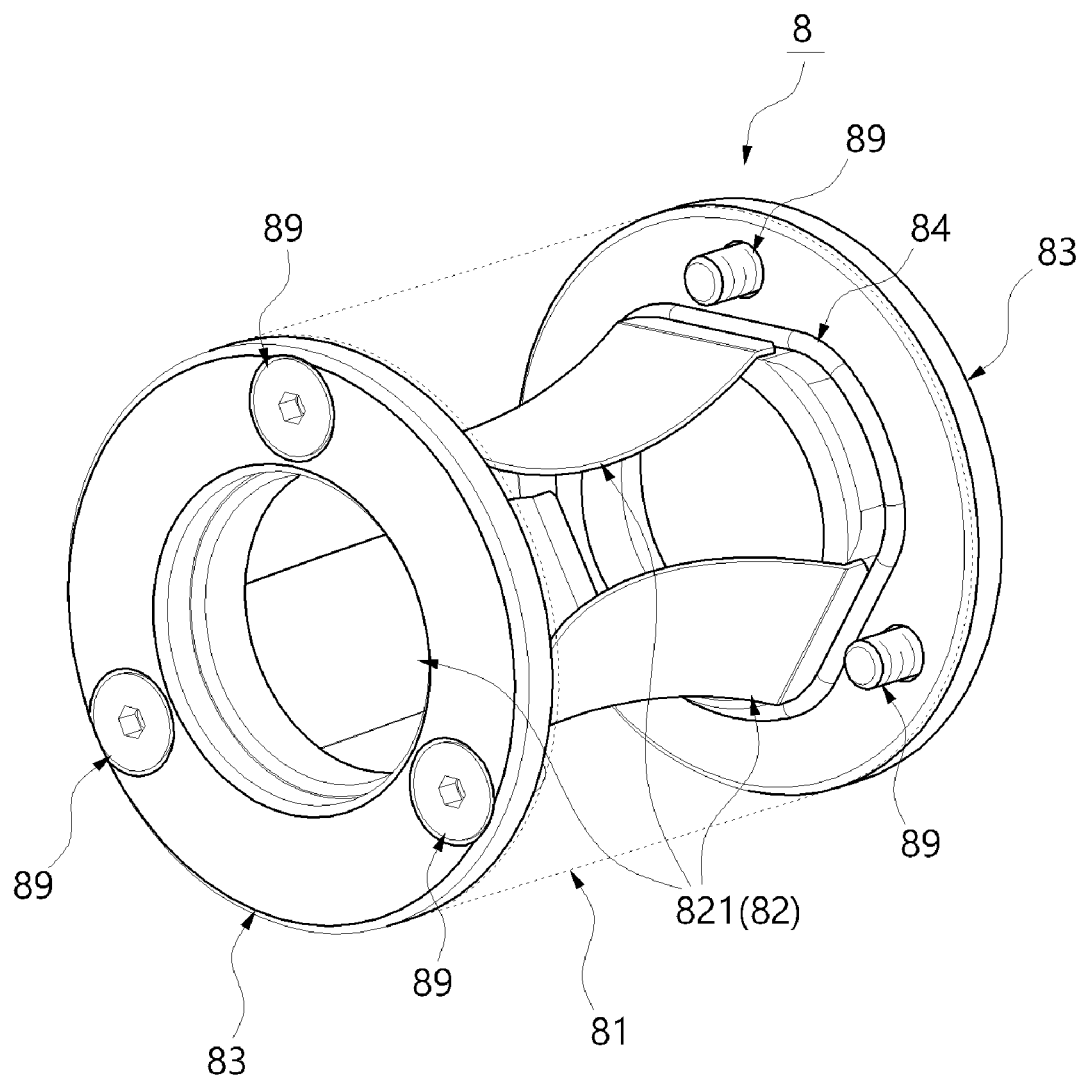
Figure 10C:
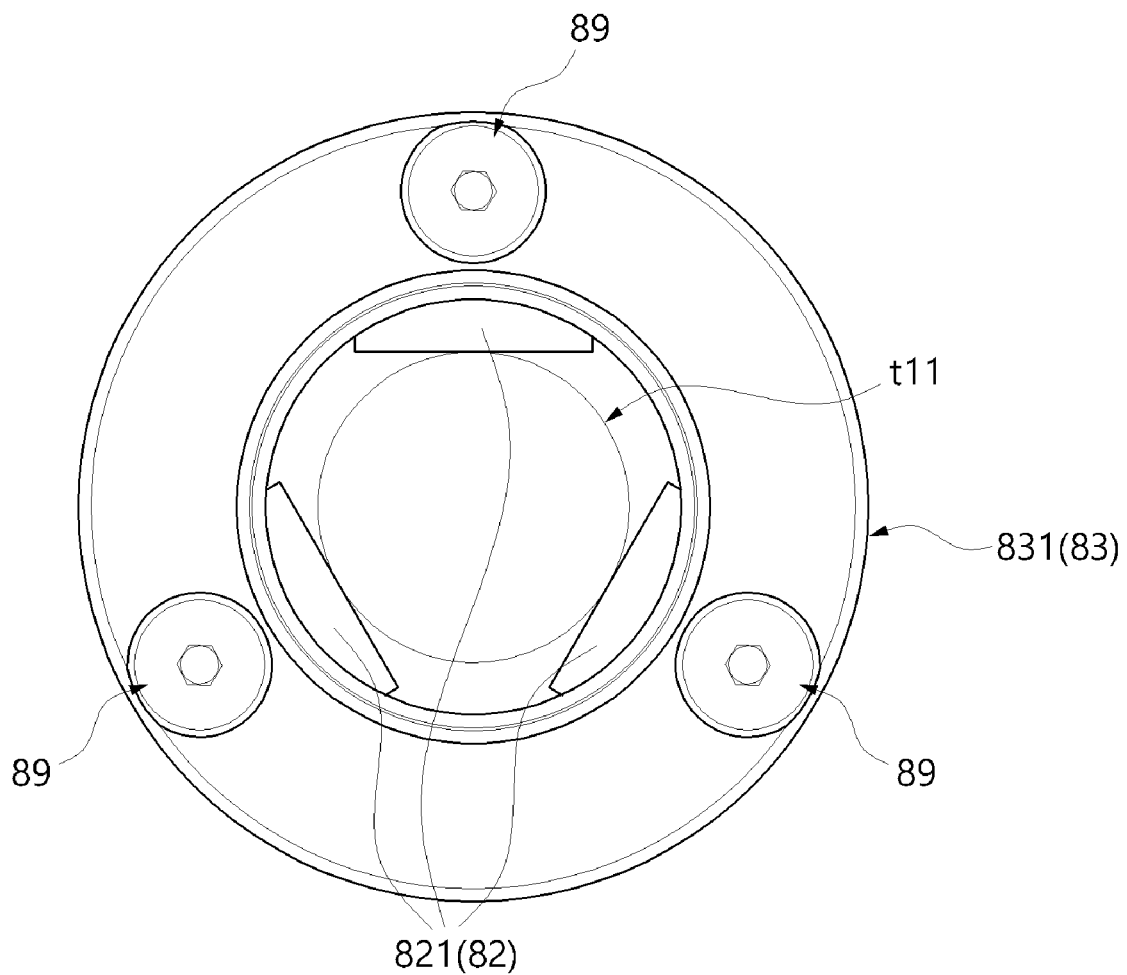
Figure 10D:
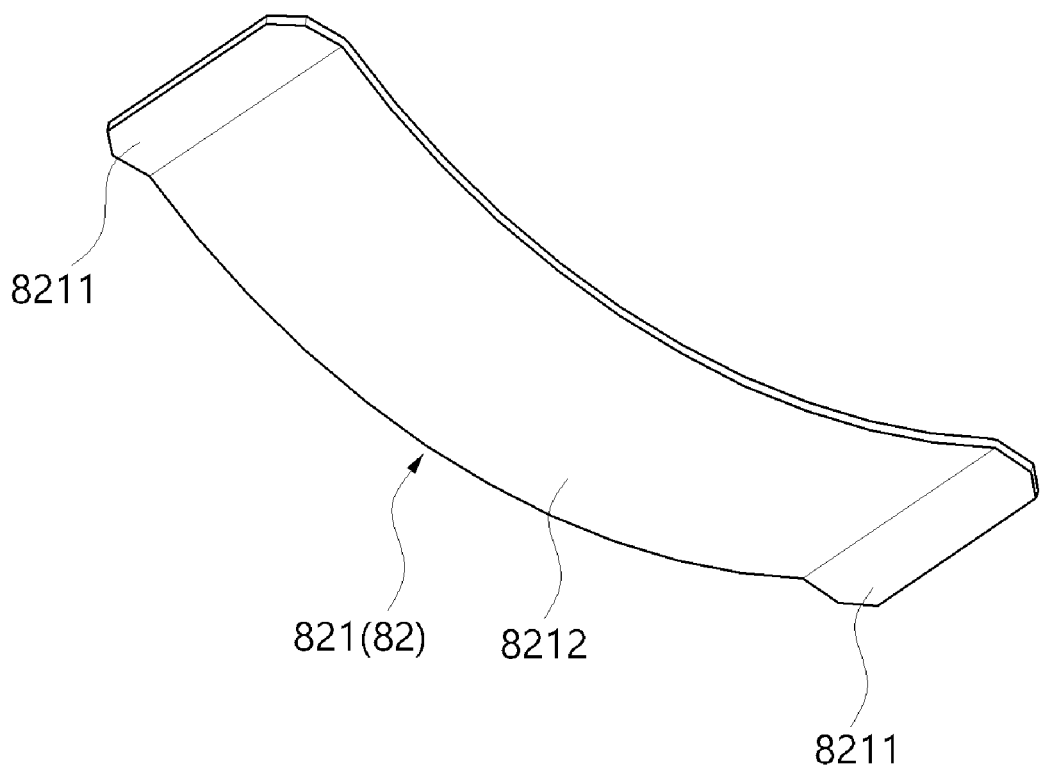
Figure 10E:
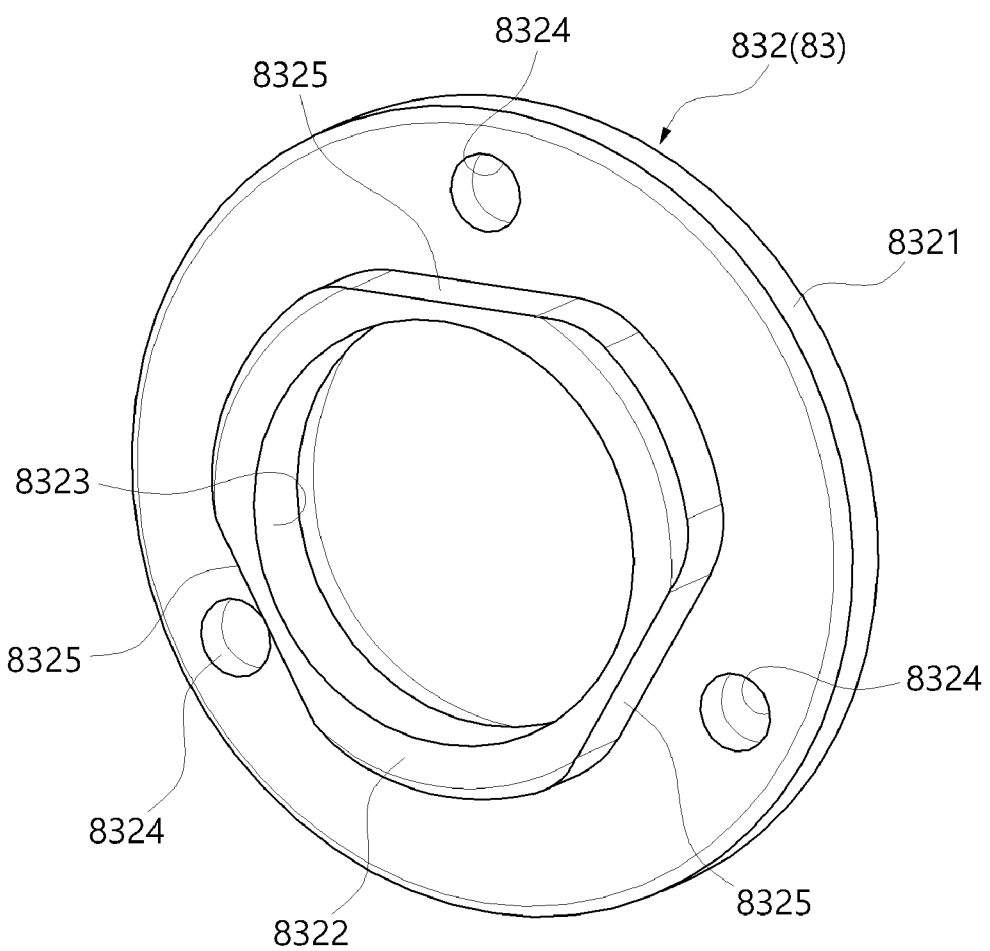
Figure 10F:
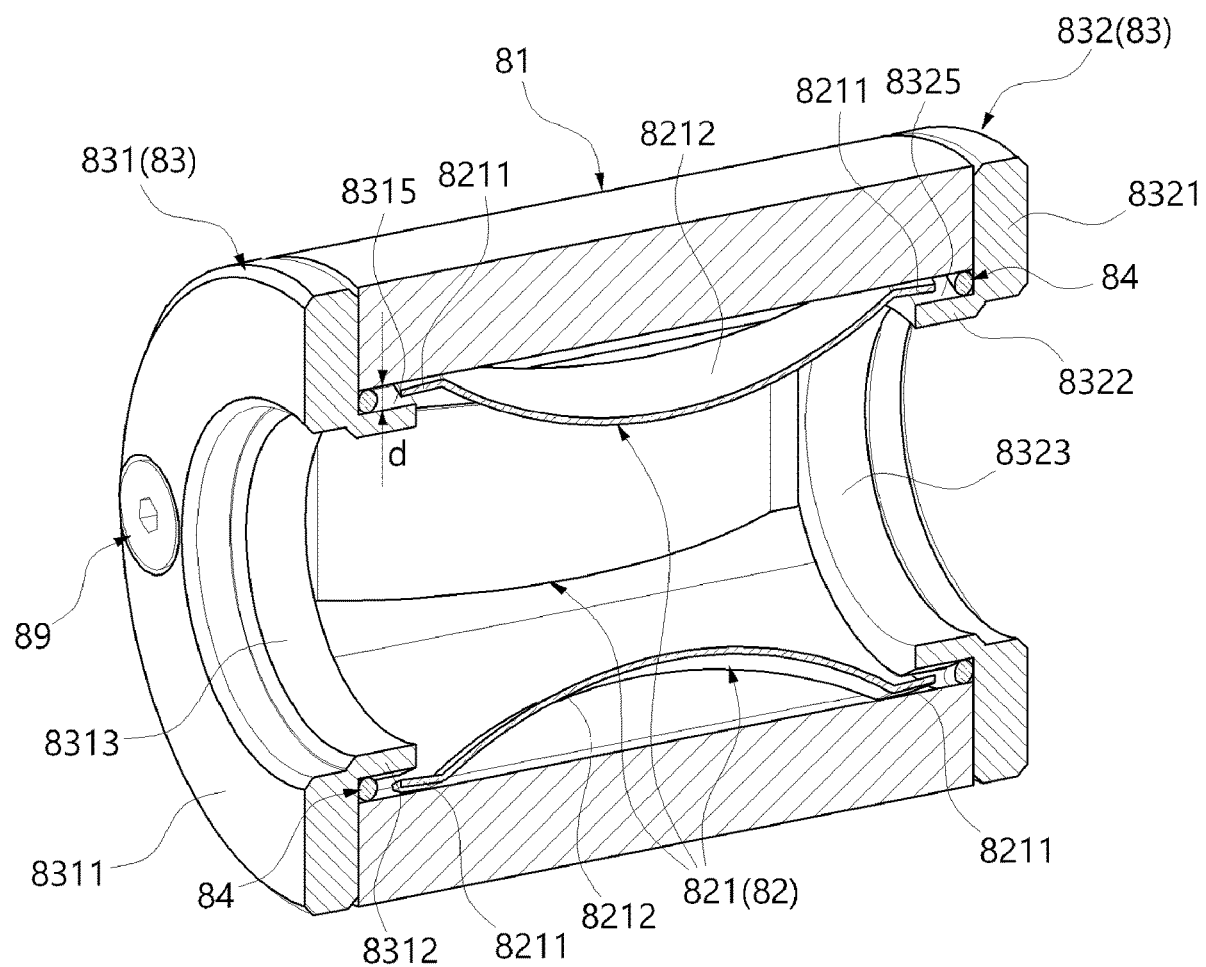
Figure 10G:
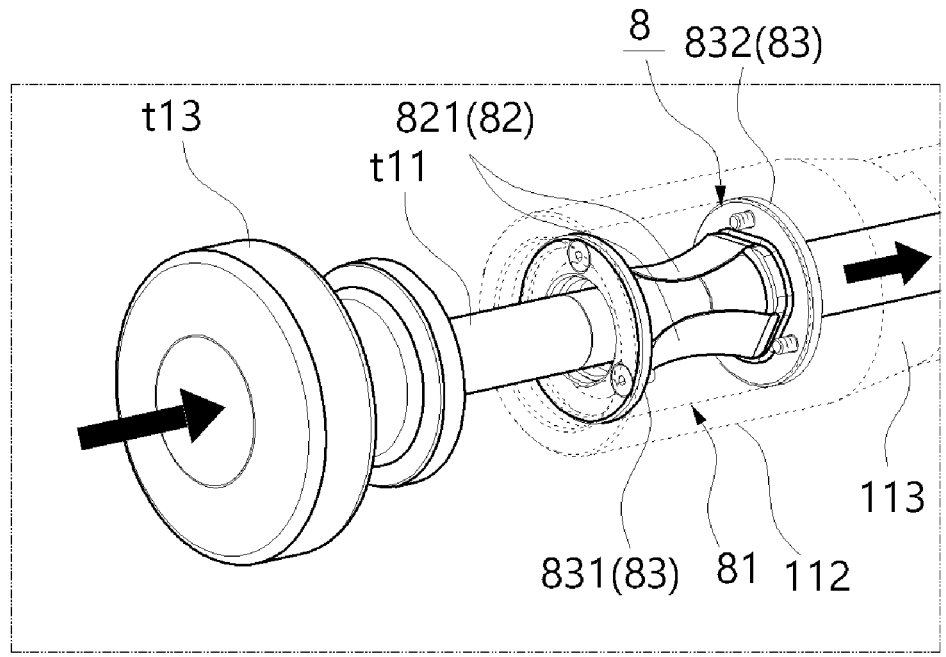
Figure 10H:
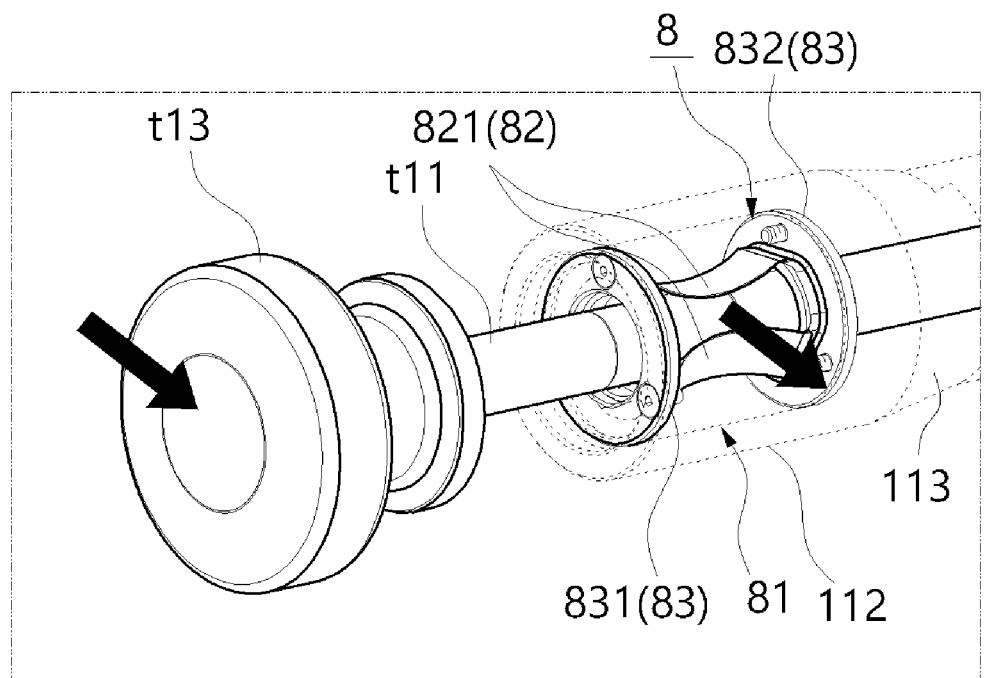

FIGS. 10A to 10H are views to illustrate a shock reduction device in a medical-surgical device having a tool movement distance display function according to an embodiment of the disclosure, in which FIG. 10A is an exploded perspective view, FIG. 10B is a perspective view to illustrate the internal structure, FIG. 10C is a lateral view, FIG. 10D is an enlarged view of an elastic member, FIG. 10E is an enlarged view of a separation preventing member, and FIG. 10F is a partial cut-open perspective view, and FIGS. 10G and 10H are views to illustrate the use states of the shock reduction device, in which FIG. 10G is a partially enlarged view to illustrate a state of when a hammer normally strikes a striking portion of an impactor, and FIG. 10H is a partially enlarged view to illustrate a state when the hammer misses the striking portion of the impactor.

Referring to FIGS. 10A to 10H, the medical-surgical device having the tool movement distance display function according to an embodiment of the disclosure includes the shock reduction device 8 installed in the shock reduction device installation portion 112 of the holder body 1 and absorbing and cushioning a shock applied to the holder body 1.

The shock reduction device 8 includes a shock reduction device body 81, a shock absorption member 82, a separation preventing member 83, and an airtight member 84, and absorbs and cushions a shock even though the shock is abnormally applied to the medical tool, thereby preventing the holder body 1, the medical tool t, etc. from being damaged or having adverse effects on surgery.

The shock reduction device body 81 refers to an element that serves as a basic frame and is installed in the holder body 1 in which the medical tool such as the impactor t1 is inserted and includes a tool insertion hole 812 in which the tool shaft t11 of the medical tool is inserted.

The shock reduction device body 81 is approximately shaped like a cylinder and is internally formed with the tool insertion hole 812 to insert the tool shaft t11 of the medical tool such as the impactor t1 therein.

The tool insertion hole 812 is shaped corresponding to the first and second separation preventing protrusions 8312 and 8322 (to be described later) so as to insert the first and second separation preventing protrusions 8312 and 8322 therein, and has an inner diameter larger than the diameter of the first and second separation preventing protrusions 8312 and 8322 so that a gap d for the insertion of the airtight member 84 and the insertion of the elastic member 821 can be formed between the tool insertion hole 812 and the first and second separation preventing protrusions 8312 and 8322. For example, the tool insertion hole 812 is formed as an approximately triangular pillar-shaped hole having three-hole flat surfaces 8121 to insert three flat springs therein, and three curved edges 8122 connecting the hole flat surfaces 8121.

In addition, the shock reduction device body 81 includes a fastening hole 815 formed on the front and rear surfaces thereof in contact with the tool insertion hole 812 to fasten a fastening screw 89 thereto.

Meanwhile, the shock absorption member 82 refers to an element that is placed in the shock reduction device body 81 and absorbs a shock applied to the medical tool and includes the elastic member 821 placed inside the shock reduction device body 81 to absorb the shock applied to the tool shaft t11.

The elastic member 821 may be formed to have various shapes and structures without specific limitations as long as it can absorb and cushion a diagonal shock transmitted from the tool shaft t11. According to this embodiment, a plurality of flat springs, which are convexedly formed to come into contact with the outer surface of the tool shaft and absorb the shock, is provided as the elastic member 821 by considering that the tool shaft t11 is shaped like a round bar.

The flat spring is structured to have locking portions 8211 formed at opposite ends thereof, and a convex portion 8212 convexedly protruding between the locking portions 8211 toward the center of the tool insertion hole 812, which may be formed by machining a rectangular plate to be bent. Further, the flat spring may be made of any material without specific limitations as long as it has elasticity. According to this embodiment, the flat spring is made of a stainless-steel sheet excellent in hygiene and durability.

Meanwhile, the separation preventing member 83 refers to an element installed in the shock reduction device body 81 to prevent the shock absorption member 82 from being separated and includes a first separation preventing flange 831 and a second separation preventing flange 832 connected to both ends, i.e., the first and second ends of the shock reduction device body 81.

The first separation preventing flange 831 is bound to the first end of the shock reduction device body 82 and includes a first binding portion 8311 formed with a through hole 8313 communicating with the tool insertion hole 812, and a first separation preventing protrusion 8312 protruding toward the inner surface of the first binding portion 8311 and supporting a first end of the flat spring not to be separated.

In addition, the first binding portion 8311 includes the through hole 8313 formed at the center of a body approximately shaped like a disc, and a plurality of fastening holes 8314 equiangularly formed to be fastened to the shock reduction device body 81.

The second separation preventing flange 832 is coupled to the second end of the shock reduction device body 81 and includes a second binding portion 8321 formed with a through hole 8323 communicating with the tool insertion hole 812 in a body approximately shaped like a disc, and a second separation preventing protrusion 8322 protruding toward the inner surface of the second binding portion 8321 and supporting the second end of the flat spring not to be separated.

Like the first binding portion 8311, the second binding portion 8321 is formed with the through hole and the plurality of fastening holes 8323 in the disc-shaped body.

The first and second separation preventing protrusions 8312 and 8322 protrude along the circumferences of the through holes 8313 and 8323 so that the gap d for inserting and accommodating the locking portion 8211 therein can be formed in the state that the first and second separation preventing flanges 831 and 832 are bound to the shock reduction device body 81.

In particular, the first and the second separation preventing protrusions 8312 and 8322 are formed with guide flat surface portions 8315 and 8325 having a flat surface structure to guide the movement of the locking portion when the flat spring contracts and expands.

The airtight member 84 refers to an element that maintains the airtightness in a connection area between the separation preventing member 83 and the shock reduction device body 81 and includes an airtight ring usually called an O-ring.

Meanwhile, the reference numeral r1 in FIG. 2 indicates an arm connector provided in the arm of the surgical robot to connect the holder support member thereto.

Below, operations of a medical-surgical device having a tool movement distance display function according to an embodiment of the disclosure will be briefly described.

Figure 11:
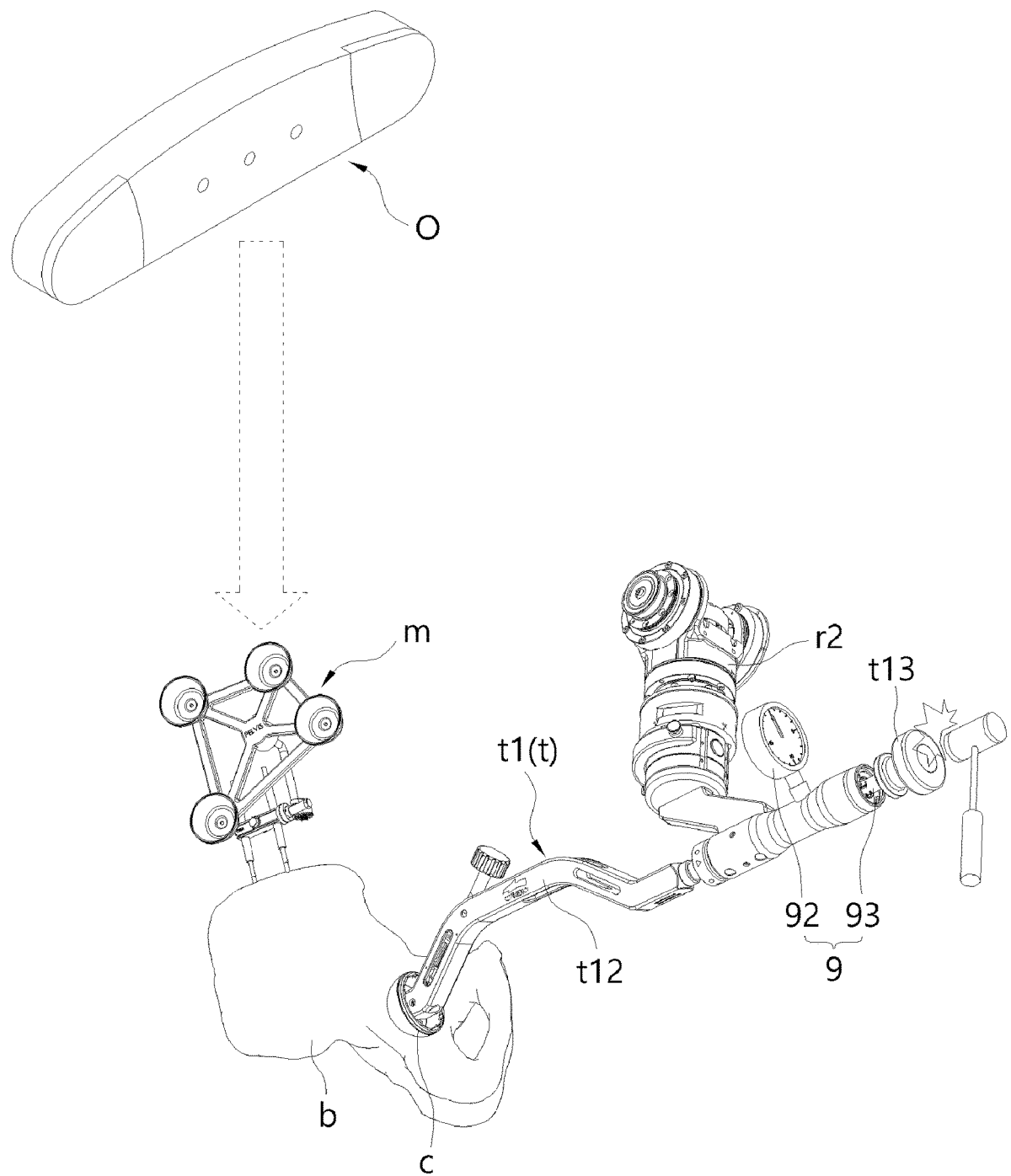
FIG. 11 is a schematic configuration view to illustrate the operations of a medical-surgical device having a tool movement distance display function according to an embodiment of the disclosure.

FIG. 11 is a schematic configuration view to illustrate operations of a medical-surgical device having a tool movement distance display function according to an embodiment of the disclosure, in which b is a pelvis bone, m is a pelvis marker installed to detect the positions of a hip joint, and o is an optical tracking system (OTS) camera to track the positions of the hip joint.

Referring to FIGS. 1 to 11, the artificial hip joint surgery is usually performed by preprocessing, such as cutting, the acetabulum of the hip joint using a reamer, inserting an artificial acetabulum cup c in the acetabulum, pressing and fixing the artificial acetabulum cup c using an impactor, and connecting an artificial femoral head to the artificial acetabulum cup c.

To this end, the holder support member 4 of the holder body 1 is first assembled to the arm of the artificial joint surgical robot, and the reamer (not shown) is mounted as the medical tool to the holder body 1 and rotated to cut the acetabulum of the hip joint.

When the preprocessing procedures such as cutting are completed, the reamer is disassembled from the holder body 1 and the impactor t1 is assembled to the holder body 1. The impactor t1 is assembled as the tool shaft t11 is inserted in the tool mounting hole 12 and bound with the tool binding unit 3, in which the locking protrusion 322 of the tool binding member 32 is aligned with the incoming groove 331 as shown in (a) in FIG. 9, inserted into the incoming groove 331 by pressing the medical tool t1 inwards as shown in (b) of FIG. 9, and rotated at an angle of approximately 30 degrees along the locking groove 332 as shown in (c) of FIG. 9, so that the locking protrusion 322 can enter the recessed end portion 333 of the locking groove 332 by the elasticity of the elastic pressurizer, thereby stably holding the medical tool t1 not to be separated.

Meanwhile, after the impactor t1 is completely assembled, the artificial acetabulum cup is installed in the front as shown in FIG. 11, and the striking portion t13 of the impactor t1 is struck using a hammer to move the tool shaft t11 in the forward direction, thereby pressing-fitting the artificial acetabulum cup c to the acetabulum of the hip joint. In this case, the holder body 1 fixed to the arm of the surgical robot is not moved, and the impactor t1 receiving the striking force is moved in a striking direction.

The surgical process of striking the impactor t1 is performed as a user applies the striking force to the striking portion t13 using the hammer as shown in FIG. 10G. When the striking direction of the hamper is aligned with the longitudinal direction, i.e., the axial direction of the impactor, the surgical procedure is stably performed. On the other hand, when the striking direction of the hamper is diagonal to (misaligned with) the axial direction of the impactor, the holder body 1 and the impactor t1 may be deformed, damaged, or destroyed. However, the shock reduction device 8 installed in the holder body 1 implements the shock absorbing function, thereby preventing these problems.

In addition, the shock absorbing function of the shock reduction device 8 is implemented in such a manner that displacement force diagonally generated in the tool shaft t11 due to the miss of the hammer as shown in FIG. 10H is applied from the outer circumferential surface of the tool shaft to the elastic member 821 and at the same time the convex portion 8212 contracts to absorb and cushion the shock because the tool shaft t11 is inserted in the tool insertion hole 812.

Meanwhile, the process of press-fitting the artificial acetabulum cup c to the acetabulum of the hip joint by striking the impactor t1 as described above is described in detail as follows. The arm of the surgical robot is moved to a surgical position calculated by surgical operating software based on the detection of the surgical robot, the position tracking camera o, and the marker m, thereby holding the impact in position. In this case, the tool shaft t11 of the impact t is adjusted in position as shown in (b) in FIG. 6 to know the distance remaining up to the set target position (see the impacting depth in FIG. 1) of the artificial acetabulum cup c to be inserted in the acetabulum of the hip joint.

In this way, when the tool shaft t11 is moved backward-by a target position, the measuring stylus 923 being in contact with the surface of the distance-detecting slope 911 is pressed down, thereby making the pointer 924 of the analog dial gauge point at the scale corresponding to the corresponding target position distance of the scale plate 925 and the scale 931 of the shaft scale portion 93 also point at the same target position distance.

In this state, a user applies the striking force to the striking portion t13 using the hammer to move the artificial acetabulum cup c including the tool shaft forward. In this case, the tool shaft is pushed backward while coming into contact with interferences (e.g., small remaining bones, skin tissue, etc.) present in an acetabular entry area of the hip joint. However, a user may repeatedly apply the striking force while checking the scales of the movement distance display unit 92 or the scales 931 of the shaft scale portion 93, thereby making the artificial acetabulum cup c to be press-fitted to and seated in the target position i (see FIG. 1).

As described above, the distance remaining up to the target position of the artificial acetabulum cup c is checkable in two ways through both the scales of the movement distance display unit 92 and the scales 931 of the shaft scale portion 93, thereby ensuring the accuracy, and making it easy for a user to check the remaining distance even though the movement distance display unit 92 implemented as the analog dial gauge is broken.

Meanwhile, in the foregoing surgical process, when the movement or motion of a patient is detected based on the position tracking camera o and the marker m, the arm position of the surgical robot may be corrected and rearranged.

The terms "comprise," "configure" and/or "have" specify the presence of stated components, unless there is a specifically different meaning in the disclosure, but do not preclude the presence thereof and should be construed to further include other components. Unless otherwise defined, all terms including technical or scientific terms used herein have the same meaning as commonly understood by those skilled in the art to which the disclosure pertains. General terms that are defined in a dictionary shall be construed to have meanings that are consistent in the context of the relevant art and will not be interpreted as having an idealistic or excessively formalistic meaning unless clearly defined in the disclosure.

In the medical-surgical device having the tool movement distance display function according to the disclosure, the movement distance indicator for indicating the movement distance is provided to indicate the movement distance of the medical tool, so that medical personnel can recognize the target movement distance of the tool accurately and quickly in the surgical process, thereby having effects on improving the accuracy of the surgery, shortening time, and improving the convenience of surgery.

In particular, the movement distance indicator allows the distance remaining up to the target position of the artificial acetabulum cup c to be checkable in a plurality of ways through the scales of the movement distance display unit and the scales of the shaft scale portion, so that medical personnel can easy check the remaining distance even though the movement distance display unit implemented as the analog dial gauge is broken, thereby having advantages of further improving the accuracy, reliability and convenience of surgery.

Although the configurations and operations of a medical-surgical device having a tool movement distance display function according to an embodiment of the disclosure have been described so far, it will be appreciated by those skilled in the art that modifications or substitutions may be made in all or part of the embodiments of the disclosure without departing from the technical spirit of the disclosure.

Accordingly, it will be understood that the scope of the disclosure falls into the appended claims and equivalents thereof.

REFERENCE NUMERALS

1: holder body 11: hollow column body
12: tool mounting hole
13: guide member installation groove
14: support member installation groove
15: tool installation groove
16: holder binding member 2: tool support unit
21: tool support guide member
3: tool binding unit
31: binding hole 32: tool binding member
33: locking portion 4: holder support member
41: holder support rod 42: connecting plate
43: arm connecting member 5: impactor holding member
7: elastic pressurizer 71: compression coil spring
72: pressurization ring 8: shock reduction device
81: shock reduction device body
82: shock absorption member
83: separation preventing member
84: airtight member
9: movement distance indicator
91: movement distance-detecting displacement portion
92: movement distance display unit
93: shaft scale portion
t: medical tool t1: impactor
t11: tool shaft

What is claimed is:

1. A surgical device having a tool movement distance display function, comprising:
   a medical tool comprising a tool shaft;
   a holder body having a tool mounting hole internally defined therein to be inserted with the medical tool therein;
   a tool support configured to support the medical tool inserted in the holder body; and
   an indicator configured to indicate a movement distance of the medical tool,
   wherein the indicator comprises:
   a displacement portion coupled to the tool shaft and configured to move in conjunction with the tool shaft; and
   a display unit configured to detect and display the movement distance of the displacement portion and the medical tool,
   wherein the displacement portion has a slope of which a diameter gradually increases in a forward direction of the medical tool, and
   wherein the display unit has a gauge and a measuring end, the display unit being disposed on the holder body so that the measuring end is configured to move in contact with the slope and the gauge is configured to display the movement distance of the displacement portion corresponding to a height of the slope.

2. The surgical device of claim 1,
   wherein the gauge comprises:
   an analog dial gauge having a stem having a spindle having a measuring stylus at an end of the spindle,
   a pointer coupled to the stem and configured to rotate based on a retraction degree of the measuring stylus, and
   a display housing having a scale plate on which the pointer rotates, or
   wherein the gauge comprises:
   a digital gauge having a stem having a measuring stylus, and
   a display configured to display digits based on a retraction degree of the measuring stylus of the digital gauge, and
   wherein the holder body has a coupling boss configured to communicate with the tool mounting hole so that the stem of the analog dial gauge or the stem of the digital gauge is disposed at a position corresponding to the displacement portion.

3. The surgical device of claim 1, wherein the indicator comprises a shaft scale portion disposed on an exposed portion of the tool shaft of the medical tool disposed in the holder body, the shaft scale portion comprising a plurality of scales.

4. The surgical device of claim 3, wherein the shaft scale portion is disposed on a surface of the tool shaft on a rear side of the holder body, and configured to set a target movement distance of the medical tool by aligning a scale of the plurality of scales corresponding to the target movement distance with a rear-end portion of the holder body.

5. The surgical device of claim 1,
   wherein the medical tool comprises an impactor configured to be used for hip joint surgery by having an artificial acetabular cup coupled to a front of the tool shaft and a striking portion disposed at a rear of the tool shaft to which striking force is applied, and wherein the tool support comprises a tool support guide to guide a movement of the tool shaft while supporting the tool shaft.

6. The surgical device of claim 5, further comprising:
a holder support coupled to the holder body,
wherein the tool mounting hole comprises:
a guide member installation groove defined on an inner circumferential surface of the tool mounting hole to seat the tool support guide therein,
a support member installation groove defined adjacent to the guide member installation groove so that a holder binding member for installation of the holder support can be installed, and
a tool installation groove defined in an end portion of the tool mounting hole on a first side to install the medical tool in the tool mounting hole.

7. The surgical device of claim 6, further comprising:
a shock reduction device disposed in the holder body to absorb and cushion a shock applied to the holder body; and
a shock reduction device insertion portion disposed at an end portion of the tool mounting hole of the holder body on a second side,
wherein the shock reduction device is disposed in the shock reduction device insertion portion.

8. The surgical device of claim 6, further comprises a tool binding unit configured to bind the medical tool inserted in the tool installation groove,
wherein the tool binding unit comprises a binding hole perforated in the holder body to communicate with an inside of the tool installation groove, a tool binding member inserted through the binding hole, and a locking portion defined in the medical tool and configured to allow the tool binding member to be inserted and locked into the locking portion.

* * * * *